(12) United States Patent
Leal et al.

(10) Patent No.: US 6,316,221 B1
(45) Date of Patent: Nov. 13, 2001

(54) FUNCTIONAL EXPRESSION OF PHEROMONE BINDING PROTEIN

(75) Inventors: Walter Soares Leal; Hubert Wojtasek, both of Tsukuba (JP)

(73) Assignee: Japan as represented by Director General of National Institute of Sericultural and Entomological Science, Ministry of Agriculture Forestry and Fisheries, Tsukuba (JP)

( * ) Notice: Subject to any disclaimer, the term of this patent is extended or adjusted under 35 U.S.C. 154(b) by 0 days.

(21) Appl. No.: 09/261,464

(22) Filed: Feb. 24, 1999

(51) Int. Cl.$^7$ .................................................. C12P 21/06
(52) U.S. Cl. ........................... 435/69.1; 530/353; 530/858
(58) Field of Search ........................... 435/69.1; 530/353, 530/858

Primary Examiner—Patrick J. Nolan
(74) Attorney, Agent, or Firm—Smith, Gambrell & Russell

(57) ABSTRACT

A method which enable to provide sufficient amount of insect OBP, and moreover, to produce on a large scale under the condition of physiological activation is proposed.

The functional expression of pheromone binding protein from *B. mori*, whereby it is expressed with *Escherichia coli* by the pET-22b vector which contains the pe1B signal peptide.

2 Claims, 3 Drawing Sheets

FUNCTIONAL EXPRESSION OF PHEROMONE BINDING PROTEIN

FIELD OF THE INVENTION

The present invention relates to the pheromone binding protein and a method for its functional expression, and more particularly to the recombinant pheromone binding protein (rPBP) of *Bombyx mori* and a method for its expression.

The recombinant pheromone binding protein (rPBP) of *Bombyx mori* is useful not only for studies of it's 3-dimensional structure and ligand binding, but also for ligand-binding protein complex and olfactory processing studies.

BACKGROUND OF THE INVENTION

Odorant binding proteins (OBP) are the most abundant components of the lymph in the antenna of insects.

These proteins are believed to participate in transport, protection and/or inactivation of information in the early events of insect olfaction.

Odorant binding proteins have been studied in Lepidoptera, where these are divided into two groups at least.

The pheromone binding proteins (PBP) belong to one group of the odorant binding proteins and have been distinguished as proteins which participate in recognition of (sex) pheromones.

Further, the proteins which belong to another group of the odorant binding proteins participate in the recognition of general odorants (general odorant binding proteins, GOBP).

The pheromone binding proteins which participate in recognition of sex pheromones have been detected and characterized in a number of species from several insects orders since the first identification of these proteins in *Antheraea pilophemus*.

Functionally, these proteins can be classified as lipocalins, a group of proteins binding hydrophobic ligands.

However, insect odor molecular binding proteins (insect OBP) share little homology with other lipocalins, which are primarily composed of 8 or 10 antiparallel β-strands forming β-barrel.

Circular dichroism measurement and theoretical structure calculation revealed that insect OBPs are in a large part α-helical.

Therefore, the study of 3-dimensional structure and that of ligand binding of insect OBPs enable to get a better understanding of the role of these proteins in the olfactory Processing.

Though reasonable Amount of functional OBP has been desired for the research in various fields, the isolation of sufficient amount of nature?? protein is out of the question.

Insect odor molecular binding proteins have been previously expressed both in bacterial and eukaryotic systems.

*Antheraea pernyi* has been expressed in the baculovirus system, but it's not a perfect method for the production of sufficient amount of insect OBP because of low yield.

While the PBP from *Antheraea polyphemus* has been expressed in low yield in *Escherichia coli*, the product is physiologically inactivated and required refolding for structural and functional studies.

Therefore, a method which enable to provide sufficient amount of insect OBP, furthermore, to overexpress under the condition of physiological activation has been in demand.

SUMMARY OF THE INVENTION

We studied said problem and found that the functional recombinant pheromone binding protein from *Bombyx mori* is successfully obtained in high yield in *Escherichia coli* by pET-22b vector which contains the pelB signal peptide, moreover, better expression efficiency is achieved at 29° C. rather than at a usual temperature (37° C.), and in the absence of the inducing agent (IPTG).

In short, means for attaining the object of invention are as follows:

(1) The functional pheromone binding protein from *Bombyx mori*, whereby it is expressed with *Escherichia coli* by the pET-22b vector which contains the N-terminal pelB signal peptide.

(2) A method for functional expression of pheromone binding protein from *Bombyx mori*, whereby it is expressed with *Escherichia coli* by the pET-22b vector which contains the N-terminal pelB signal peptide.

(3) A method for functional expression of the pheromone binding protein from *Bombyx mori*, whereby it is expressed with *Escherichia coli* by the pET-22b vector which contains the N-terminal pelB signal peptide, in between 36–38° C., further preferably in between 28–30° C.

(4) A method for functional expression of pheromone binding protein from *Bombyx mori*, whereby it is expressed with *Escherichia coli* by the pET-22b vector which contains the N-terminal pelB signal peptide in between 36–38° C., further preferably in between 28–30° C., and in the absence of the inducing agent (IPTG).

The recombinant protein of the present invention efficiently bound to the radiolabeled pheromone (bombykol) in native gel electrophoresis assay.

According to the present invention, it is possible to express sufficient amount of insect OBP, moreover the production under the condition of physiological activation is also enabled.

BEST MODE FOR CARRYING OUT THE INVENTION

Figure 1:
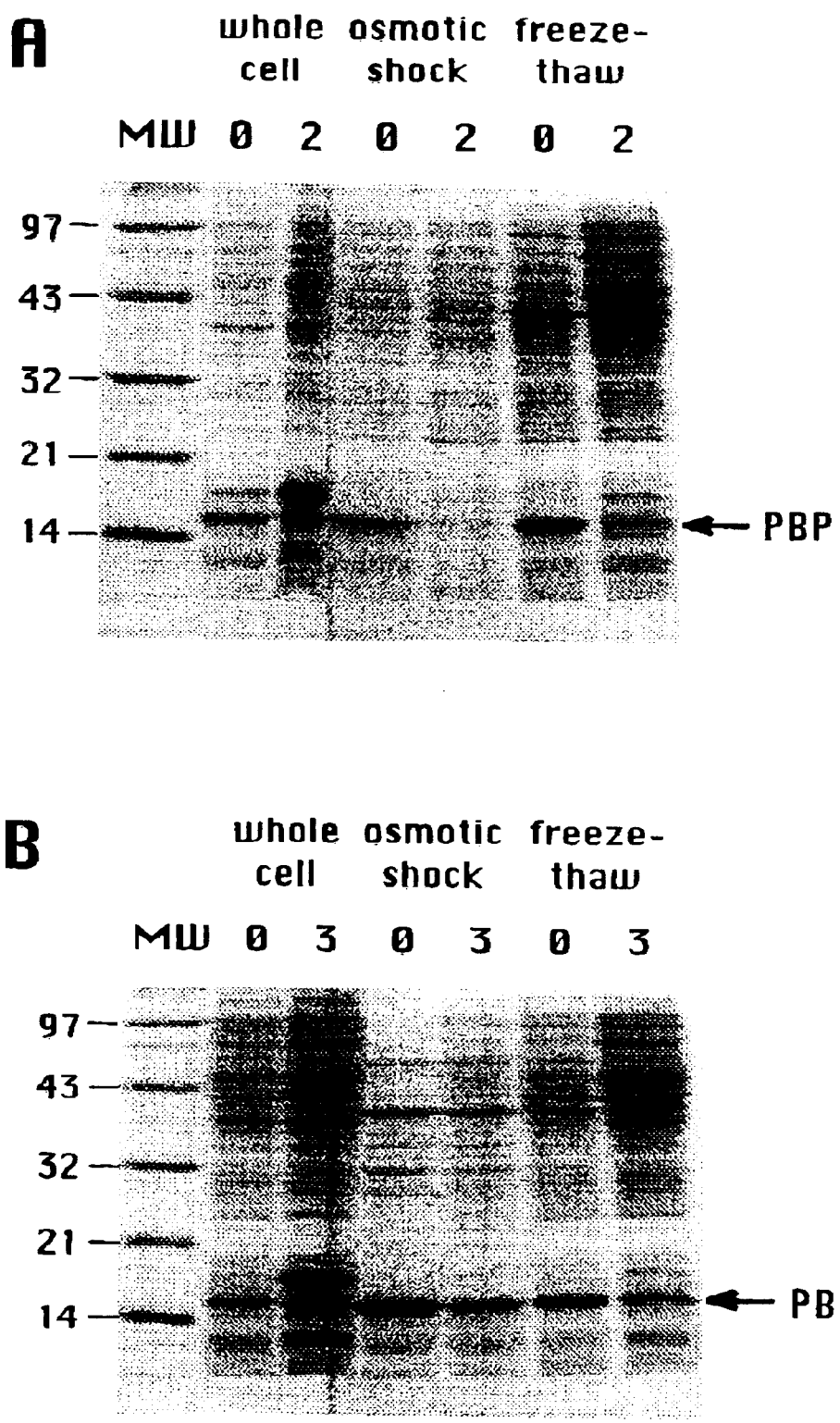
FIG. 1. Expression of *B. mori* PBP at 37° C. (A) and 29° C. (B). Samples were taken before induction (0) and at time points indicated (2 h 37° C. or 3 h at 29° C.)

This invention is further discussed below in detail by making reference to examples. The technical scope of this invention is not, however, limited by the explanation which will be discussed below.

[Materials and Methods]

1. Molecular Cloning and Preparation of Recombinant Vectors

RNA was isolated by a single step acid-guanidinium-phenol-chloroform extraction from antennae of 20 *B. mori* males.

PolyATtract (Promega) was used to purify mRNA, and cDNA strand was synthesized with AMV reverse transcriptase (Promega) and an oligo(dT) primer.

Reverse transcriptase was inactivated at 70° C. for 10 min, the reaction mixture was diluted 20-fold, and approximately 1 ng of the cDNA was used for DNA amplifier reaction (PCR).

The following primers were designed based on the published sequence of *B. mori* PBP:

SEQ ID NO1 CGTCTCAAGAAGTCATGA (5'-primer, blunt-end ligation into Msc I site), SEQ ID NO:2 AGACACTCGAGATTCTCAAACTTCAGCT (3'-primer for the plain construct, Xho I site is underlined), and SEQ ID NO:3 ACAGAGTCGACTTCAGCTAAAATTTCTCC (3'-primer for the HisTag construct, Sal I site, compatible with Xho I, and preserving the C-terminal valine is underlined).

Polymerase chain reactions were carried out in a Mini-Cycler (PTC-150, MJ Research) using Pfu DNA Polymerase (Stratagene) in 50 mM Tris-HCl, pH 8.5, 15 mM $(NH_4)_2SO_4$, 15 mM $MgCl_2$ with annealing at 50° C.

PCR products were digested with Xho I or Sal I, purified from low-melting-point agarose by GeneClean (Bio101), and ligated into pET22b (Novagen), which had been predigested with Msc I and Xho I and purified in the same way.

Ligation reaction was used for transformation of Epicurian *E. coli* MRF' Kan cells (Stratagene) and colonies containing the recombinant vector were identified by PCR.

Plasmids were isolated and the constructs were sequenced with T7 promoter and T7 terminator primers, using Dye Terminator Reaction Ready Kits (Perkin Elmer) on an ABI PRISM model 373A automated DNA sequencer (PE Applied Biosystems).

2. Expression of the Recombinant Proteins

Recombinant vectors with verified sequences were transferred into expression hosts BL21 (DE3) or BL21 (DE3) pLysS (Novagen).

Single colonies were used to inoculate liquid media (LB with 50 μg/ml of carbenicillin) and grown overnight at 37° C. or for 24 hours at 29° C.

Cultures were then diluted to $OD_{550}=0.8$, aliquots of preinduced cultures were taken, and IPTG was added to 1 mM final concentration.

Additional aliquots were taken 2 and 3 hours (37° C.), or 3 and 5 hours (29° C.) after induction.

Periplasmic proteins were released by osmotic shock, as described by the manufacturer (Novagen).

Alternatively, the soluble proteins were liberated by sonication or freeze-thaw cycles.

All samples were analyzed by SDS and nonSDS PAGE taking *B. mori* male antennal extracts as a control.

3. Purification and Characterization of the Recombinant Proteins

Tris-HCl, pH 8.0 was added to the periplasmic fraction to 20 mM final concentration and the sample was loaded onto a MonoQ column (HR 5/5, Pharmacia).

Proteins were eluted with a linear gradient of 0–400 mM NaCl in 10 mM Tris-HCl, pH 8.0 using the Pharmacia FPLC system.

Fractions containing the recombinant PBP were pooled (5 ml), applied to a gel filtration column (Sephacryl S-100 HR, Pharmacia, 2.5×50 cm) preequilibrated with 10 mM Tris-HCl, pH 8.0 and the proteins were eluted with the same buffer at 25 ml/hour.

The N-terminal sequence of the purified PBP was determined on a Beckman LF 300 PS gas phase peptide sequencer with PTH analysis on Beckman System Gold HPLC.

Molecular weight of the recombinant protein was measured by MALDI-TOF mass spectrometry (Voyager, PerSeptive Biosystems) in a positive ion mode with 3,5-dimethoxy-4-hydroxycinnamic acid as a matrix.

Activity of the recombinant protein was tested by binding assay with labeled bombykol following published procedures.

[Results and Discussion]

We have selected the pET-22b vector, which contains the N-terminal pelB signal peptide directing the expressed proteins into the *E. coli* periplasm.

This provides appropriate oxidative environment for formation of disulfide bonds.

Insect PBPs are secreted proteins and existence of 2 or 3 disulfide bonds have been postulated.

Periplasmic expression has been successful in the case of the serum retinol-binding protein, whose size, function, and properties resemble those of PBPs.

PBP also possesses 3 disulfide bonds, unlike most proteins from the lipocalin family.

The lipocalin family lack such linkages.

Using this expression system we have achieved high level of expression for both rPBP of *B. mori* rPBP and the His-Tagged version in the standard host BL21 (DE3) (FIG. 1).

FIG. 1 shows the expression of *B. mori* PBP at 37° C. (A) and 29° C. (B).

The following samples were separated on a 15% SDS-polyacrylamide gel: whole cell pellet (100 μl culture-equivalent) and the soluble proteins released by osmotic shock or freeze-thaw cycles (500 μl culture-equivalent).

Samples were taken before induction (0) and at time points indicated (2 hours at 37° C. or 3 hours at 29° C.).

There was further drop in yield of soluble protein after longer incubation time (3 hours at 37° C. or 5 hours at 29° C.).

Our nucleotide sequence differed in four positions (in all 6 clones sequenced) from the published sequence, but these substitutions did not introduce any changes of the amino acid sequence of the protein.

There was a substantial level of expression even before the induction with IPTG.

After the induction, two highly expressed bands appeared, and the amount of the total recombinant protein, when expressed at 37° C., raised to 40–50 mg/l.

However, transfer to the periplasm was dramatically reduced after the induction, and a higher yield of soluble protein was obtained in the absence of IPTG.

Under these conditions (37° C., preinduced culture) only 10–20% (<2 mg) was released from the periplasmic fraction by osmotic shock (FIG. 1A).

Sonication and freeze-thaw cycles were more efficient but these methods also released much higher amount of bacterial proteins (FIG. 1), which would make the purification protocol more elaborate, thus reducing the final yield.

The HisTag construct did not provide any advantage in terms of purification efficiency and its further expression was therefore not pursued.

It is a generally known phenomenon that expression at lower temperatures, even though it significantly reduces the total amount of recombinant protein, increases the proportion of the soluble protein.

Slower production of the recombinant protein provides better conditions for proper protein processing and folding, giving sufficient time to cellular proteases and chaperones.

We therefore tested the expression of *B. mori* PBP at 29° C.

In the absence of the inducing agent the amount of the recombinant protein was not significantly reduced, as compared to 37° C.

Now, however, almost all of it (>80%) was produced in the soluble form, directed to the periplasm (FIG. 1B).

Figure 2:
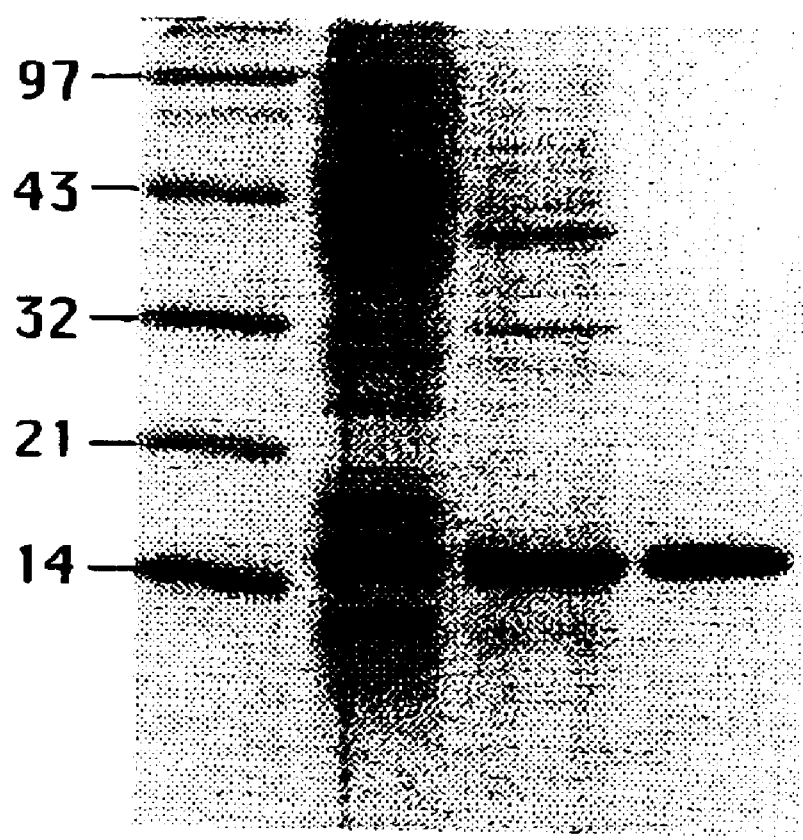
FIG. 2. Purification of the recombinant protein. Approximately equal amounts of the recombinant protein in whole cell lysate (WC), periplasmic Fraction (Per) or in pure form (Pure) were separated on a 15% SDS-polyacrylamide gel.

The recombinant protein accumulated, when the cultures were grown to higher density ($OD_{550}$=1.6), and such conditions were used for large scale expression (FIG. 2).

FIG. 2 shows the purification data of the recombinant protein of the present invention.

The culture was grown to late log phase, periplasmic proteins were released by osmotic shock and purified by ion exchange (MonoQ) and gel filtration (Sephacryl S-100 HR) chromatography.

Approximately equal amounts of the recombinant protein in whole cell lysate (WC), periplasmic fraction (Per) or in pure form were separated on a 15% SDS-polyacrylamide gel.

Approximately 8 mg of the soluble recombinant protein per liter could be isolated by osmotic shock in a relatively pure form and complete purification (>99%) was easily achieved in 2 steps (FIG. 2).

N-terminal sequencing determination and mass spectrometry showed that the lower band, expressed during the preinduced phase and directed into the periplasm, was the properly processed protein, without the pelB signal peptide.

The molecular weight determined for the plain protein was 15,888 Da (calculated 15,884 Da) and 16,843 for the His-Tag construct (calculated 16,836 Da).

The lower band obtained from the plain construct (equivalent to the native protein) also comigrated with *B. mori* PBP from antennal extracts on nonSDS gel.

Slow expression of the target protein in the absence of the inducing agent provided sufficient time for proper processing and targeting of the recombinant protein into the periplasm.

Significant expression of the recombinant protein before induction was also observed for the general odor molecular binding protein from *Manduca sexta*, when expressed intracellularly in the pHN1+ vector.

Such expression in the absence of the inducing factor may therefore be a more general feature for these proteins, and in combination with the periplasmic targeting may provide efficient method for their production in *E. coli*.

Periplasmic localization also circumvents the degradation of recombinant proteins experienced, for example, in the case of *M. sexta* GOBP1.

We therefore conclude that the periplasmic expression system may be generally applicable for expression of this class of proteins in *E. coli*.

To test the activity of the recombinant protein we performed binding assays with the labeled pheromone.

The protein efficiently bound the isotope ligand, which indicated that it was properly folded and pysiologically activated.

Figure 3:
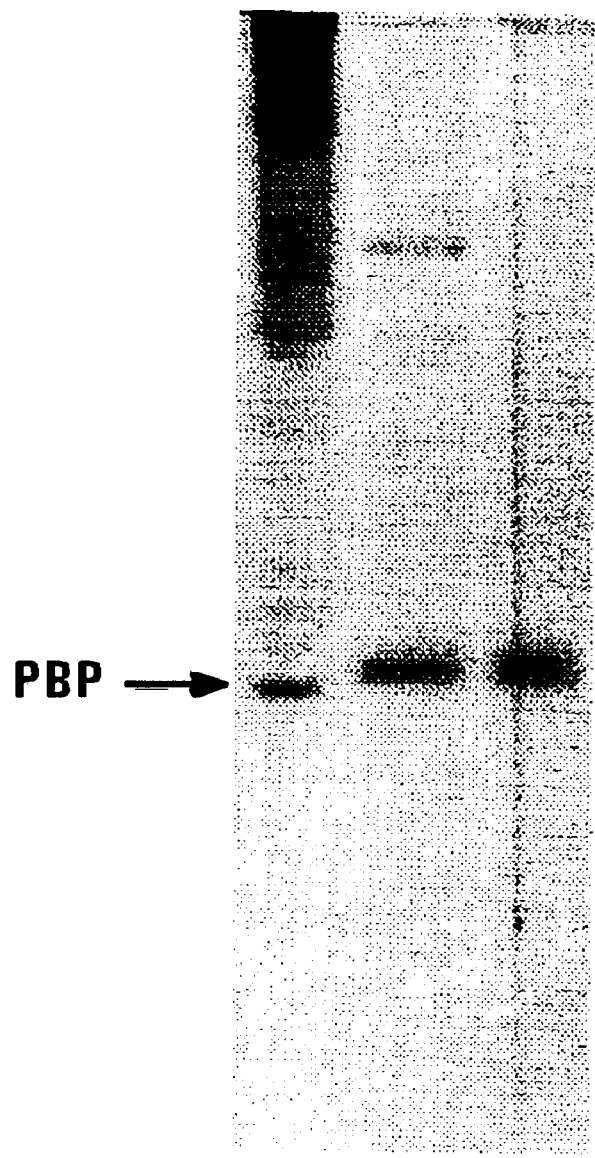
FIG. 3. Binding of the radioactive bombykol by *B. mori* PBD. The recombinant protein (ca. 2 $\mu$g), either in the periplasmic fraction (Per) or purified (Pure) were incubated with 10 $\mu$Ci of boubykol. They bound the radidabeled pheromone with high affinity. The protein extract from male Antennae (Ant) is used as control in the native gel separation.

FIG. 3 shows the binding assay of the recombinant protein, either in the periplasmic fraction (Per) or purified (Pur) fractions. The recombinant protein comigrated with the native pheromone binding protein (PBP).

SEQUENCE LISTING

<160> NUMBER OF SEQ ID NOS: 3

<210> SEQ ID NO 1
<211> LENGTH: 18
<212> TYPE: DNA
<213> ORGANISM: B. mori PBP

<400> SEQUENCE: 1
cgtctcaaga agtcatga                                                  18

<210> SEQ ID NO 2
<211> LENGTH: 28
<212> TYPE: DNA
<213> ORGANISM: B. mori PBP

<400> SEQUENCE: 2
agacactcga gattctcaaa cttcagct                                       28

<210> SEQ ID NO 3
<211> LENGTH: 29
<212> TYPE: DNA
<213> ORGANISM: B. mori PBP

<400> SEQUENCE: 3
acagagtcga cttcagctaa aatttctcc                                      29

The second, higher band was therefore the unprocessed pre-protein with the signal peptide.

Apparently, the rapid production of the target protein exceeded the capacity of the signal peptidase.

What is claimed is:

1. A method for functional expression of pheromone binding protein, comprising expressing pheromone binding protein obtained from *Bombyx mori* with *Escherichia coli* by the pET-22b vector which contains the N-terminal pe1B signal peptide, wherein said pheromone binding protein has a molecular weight of about 15 kDa, as determined by 15% SDS-polyacrylamide gel, and binds bombykol.

2. Pheromone binding protein, whereby the protein is produced according to the method of claim 1, wherein said pheromone binding protein has a molecular weight of about 15 kDa, as determined by 15% SDS-polyacrylamide gel, and binds bombykol.

* * * * *